United States Patent [19]
Miller et al.

[11] Patent Number: 5,912,339
[45] Date of Patent: Jun. 15, 1999

[54] OLIGONUCLEOSIDE ALKYL OR ARYLPHOSPHONATE DERIVATIVES CAPABLE OF CROSSLINKING WITH OR CLEAVING NUCLEIC ACIDS

[75] Inventors: Paul S. Miller, Baltimore; Paul O.P. Ts'o, Lutherville, both of Md.

[73] Assignee: The Johns Hopkins University, Baltimore, Md.

[21] Appl. No.: 08/342,005

[22] Filed: Nov. 16, 1994

Related U.S. Application Data

[63] Continuation of application No. 07/558,338, Jul. 27, 1990, abandoned, which is a continuation-in-part of application No. 06/924,234, Oct. 28, 1986.

[51] Int. Cl.$^6$ ................................................. C07H 21/02
[52] U.S. Cl. .................... 536/24.5; 536/24.3; 514/44; 435/6
[58] Field of Search .............................. 536/24.5; 514/44; 435/6

[56] References Cited

U.S. PATENT DOCUMENTS

| | | | |
|---|---|---|---|
| 4,469,863 | 9/1984 | Ts'o et al. | 536/24.5 |
| 4,511,713 | 4/1985 | Miller et al. | 435/6 |
| 4,582,789 | 4/1986 | Sheldon et al. | 435/6 |
| 4,757,055 | 7/1988 | Miller et al. | 514/44 |
| 4,835,263 | 5/1989 | Nguyen et al. | 536/24.3 |

FOREIGN PATENT DOCUMENTS

| | | | |
|---|---|---|---|
| 0117777 | 9/1984 | European Pat. Off. | 536/24.5 |
| 0169787 | 1/1986 | European Pat. Off. | 536/24.5 |
| 2568254 | 1/1984 | France | 536/24.5 |
| 8301223 | 3/1984 | France | 536/24.5 |

OTHER PUBLICATIONS

Letsinger et al., "Effects of Pendant Groups at Phosphorus on Binding Properties of d–ApA Analogues," *Nucleic Acids Research*, 14(8), 3487–3499 (1986).

Thuong et al., "Chemical Synthesis of Natural and Modified Oligodeoxynucleotides," *Biochemie*, 67, 673–684 (1985).

Lee et al., "Interaction of Psoralen–Derivatized Oligodeoxyribonucleoside Methylphosphonates with Single–Stranded DNA," *Biochemistry*, 27(9), 3197–3203 (1988).

Webb et al., "Hybridization Triggered Corss–Linking of Deoxyoligonucleotides," *Nucleic Acids Res.*, 14(19), 7661–7674 (1986).

Dreyer et al., "Sequence–specific Cleavage of Single–stranded DNA: Oliodeoxynucleotide–EDTA •Fe(II)," *Proc. Nat. Acad. Sci. USA*, 82, 968–972 (1985).

Chu et al., "Non–enzymatic Sequence–specific Cleavage of Single–stranded DNA," *Proc. Nat. Acad. Sci. USA*, 82, 963–972 (1985).

Helene et al.(III), "Oligonucleotides Covalently Linked to Interacting Agents: A New Class of Gene Regulatory Substances," *Biochemie*, 67, 777–783 (1985).

Asseline et al., "Nouvelles Subsances a Forte Affinite Specifique pour des Sequences D'acides Nucleiques: Oligodesoxynucleotides lies de Facon Covalent a un Agent Intercalant," *Compt. Rend. Acad. Sci. Paris. Series III*, 297, 369–372 (1983).

Hashimoto et al., "Synthesis of Porphyrin(Fe)–Intercalators which Cause DNA Scission," *Tett. Lett.*, 24(14), 1523–1526 (1983).

R. S. Root–Bernstein(I), "AIDS Is More Than HIV: Part I," *Genetic Engineering News*, Sep. 1, 1992, pp. 4–6.

R. S. Root–Bernstein(II), "AIDS IS More Than HIV: Part II," *Genetic Engineering News*, Sep. 15, 1992, pp. 4–5.

Zon, "Oligonucleotide Analogues as Potential Chemotherapeutic Agents," *Pharmaceutical Research*, 5(9), 539–549 (1988).

Kulka et al., "Antiviral Effect of Oligo(Nucleoside Methylphosphonate) Complementary to the Herpes Simplex Virus Type 1 Immediate Early mRNAs 4 and 5," *Antiviral Research*, 20, 115–130 (1993).

Krieg et al., "CpG Motifs in Bacterial DNA Trigger Direct B–Cell Activation," *Nature*, 374, 546–549 (Apr. 6, 1995).

T. Gura, "Antisense Has Growing Pains—Efforts to Develop Antisense Compounds as Therapies for Cancer, AIDS, and Other Diseases Have Encountered Some Unexpected Questions About How the Drugs Really Work," *Science*, 270, 575–577 (1995).

*Primary Examiner*—John Kight
*Assistant Examiner*—L. Eric Crane
*Attorney, Agent, or Firm*—Cushman Darby & Cushman; IP Group of Pillsbury; Madison & Sutro

[57] ABSTRACT

A composition for inactivating a target nucleic acid which comprises an oligonucleoside alkyl or arylphosphonate analogue which is complementary to the sequence of the target nucleic acid and includes a functional group which reacts with the target nucleic acid to render the target nucleic acid inactive or nonfunctional.

1 Claim, 9 Drawing Sheets d-A$_p$T$_p$G$_p$C

N  5'————————A-A-A-A-U-G-U-C-U-G-U-U-A-C-A————————3'
          3'-TpApCpApGpApCpA-'5 ANTI N

NS 5'————————A-U-C-A-U-G-G-A-U-A-A-U-C-U-C————————3'
          3'-TpApCpCpTpApTpTpA-'5 ANTI NS

G  5'————————A-C-U-A-U-G-A-A-G-U-C-G-C-U-U————————3'
          3'-TpApCpTpTpCpApCpG-'5 ANTI G

General structure of an EDTA-$Fe^{2+}$-derivatized oligonucleoside methylphosphonate.

Synthetic scheme for the preparation of EDTA-Fe$^{2+}$ modified oligonucleoside methylphosphonates Hydrolysis of rabbit globin mRNA by EDTA-Fe$^{2+}$ modified d-TpGCACCAT.

OLIGONUCLEOSIDE ALKYL OR ARYLPHOSPHONATE DERIVATIVES CAPABLE OF CROSSLINKING WITH OR CLEAVING NUCLEIC ACIDS

RELATED APPLICATION

This is a continuation of application Ser. No. 07/558,338, filed on Jul. 27, 1990, which was abandoned upon the filing hereof which is a continuation-in-part of Ser. No. 06/924,234, filed Oct. 28, 1986.

The work disclosed herein was supported by grants from the National Institute of Health and the Department of Energy.

The present invention is concerned with certain novel derivatives of oligonucleoside alkyl or aryl phosphonates and uses thereof.

the work disclosed herein was supported by grants from the national Institute of health and the Department of Energy.

BACKGROUND TO THE INVENTION

We have previously disclosed the preparation of oligodeoxyribonucleoside alkyl or arylphosphonates. See, for example, our U.S. Pat. Nos. 4,469,863 and 4,507,433 and U.S. application Ser. No. 605,451, filed Apr. 30, 1984. We have also described the use of these oligonucleoside alkyl or arylphosphonates for controlling or interfering with the effect or function of foreign nucleic acid. See, for example, our U.S. Pat. No. 4,511,713 and Ser. No. 604,919 filed Apr. 27, 1984.

The contents of these patents and applications are incorporated herein by reference.

In the above mentioned U.S. Pat. No. 4,511,713 and Ser. No. 604,919, we have described a process for selectively controlling or interfering with the effect or function of foreign nucleic acid by determining the base sequence for the nucleic acid and then binding the nucleic acid with an appropriately prepared nonionic oligonucleoside alkyl or arylphosphonate analogue which has a base sequence complementary to the indicated sequence of the foreign nucleic acid. The analogue can be used to control protein synthesis caused by the foreign nucleic acid, or the replication and expression of the foreign nucleic acids. These analogues may also be used to control virus messenger RNA translation or pre-messenger RNA processing. Inhibition of the Herpes simplex virus (type 1 and type 2) is also disclosed.

BRIEF DESCRIPTION OF THE INVENTION

The present invention is concerned with the provision of derivatives of the previously disclosed oligonucleoside alkyl or arylphosphonates, especially oligonucleoside methyl phosphonates, which include one or more functional groups that can react with a targeted nucleic acid to render the same nonfunctional or inactive. The reaction may involve crosslinking with the nucleic acid, cleaving the acid or the like. In any case, the nucleic acid is rendered ineffective and thus controlled by the combination of a reactive functional group attached to complementary oligomers. While the parent (underivatized) oligomers are themselves effective for controlling selected nucleic acids as previously described, the derivatives contemplated herein have been found to be more effective than the parent oligomers as evidenced, for example, by the fact that the derivatives can be used in substantially smaller amounts to obtain equivalent inhibitory effects.

The derivatives of the invention may be broadly described as oligonucleoside alkyl or arylphosphonates which have a base sequence that is complementary to the base sequence of the targeted nucleic acid of concern and which includes a functional group reactive with the targeted nucleic acid to render the same targeted nucleic acid inactive or nonfunctional. Preferably the oligomer is an oligonucleoside methyl phosphonate although other alkyl or arylphosphonates may be used.

A wide variety of functional groups are contemplated for use herein. According to one advantageous embodiment, the functional group is photoreactable, e.g. activated by ultraviolet light, for reaction with the nucleic acid so as to effect the desired crosslinking between the oligomer and the nucleic acid. Alternatively, the functional group is one which cleaves the nucleic acid. In another alternative, the functional group may be an alkylating agent which on reaction separates from the oligomer and attaches to the targeted nucleic acid to render the same nonfunctional. In all of these embodiments, the oligomer, with its base sequence complementary to the nucleic acid of interest, binds itself to the targeted nucleic acid and so positions its functional group as to enable the group to effectively react in one way or another with the nucleic acid to inactivate the same.

The positioning of the functional group on the oligomers may be varied. For example, it may be positioned at an end of the oligomer or intermediate the ends as may be most advantageous in the circumstances and taking into account the nature of the nucleic acid. A plurality of functional groups may also be included on the oligomer although this is not usually necessary.

Representative of the embodiment of the invention where crosslinking occurs are derivatives of oligodeoxyribonucleoside methylphosphonates modified to include an aminomethyltrimethyl psoralen group (AMT). This group is photoactivatable but it will be appreciated that other crosslinking groups, which may or may not be photoreactable, Ray be used in lieu of the psoralen group.

A typical derivative for cleaving the nucleic acid is a transition metal chelating complex, e.g. ethylene diamine tetracetate (EDTA) or derivative thereof. However, cleaving groups other than EDTA are also contemplated e.g. phenanthroline, porphyrin or bleomycin.

The invention is applicable to any type of nucleic acid including double stranded DNA. However, it is of particular advantage for use with RNA, especially messenger RNA (mRNA) and pre-messenger RNA (pre-mRNA).

DESCRIPTION OF THE DRAWINGS

Various aspects of the invention are illustrated in the accompanying drawings wherein:

With more specific reference to the drawings, FIG. 1 illustrates a typical oligonucleotide analog which prior work has shown can be taken up intact by cells and which can be derivatized for purposes of the present invention. As shown in FIG. 1, these analogs contain a 3'–5' linked methylphosphonate internucleotide bond which replaces the phosphodiester bond found in naturally occurring nucleic acids. The methylphosphonate group is non-charged. As a result, the oligomer is quite lipophilic and is able to penetrate the plasma membrane of cells. The methylphosphonate linkage is also resistant to nuclease hydrolysis and therefore the oligomers have very long halflives in cell culture medium and inside cells. Previous studies with analogs ranging from three to seven nucleoside units in length have shown that they can inhibit tRNA aminoacylation and mRNA translation in cell-free systems, and that they can selectively inhibit protein synthesis in permeable E.coli cells. See Biochemistry 20, pages 1874–1880 (1980) and Proc. Natl. Acad. Sci. 78, pages 1537–1541 (1981). Solid phase synthetic procedures are known which permit the synthesis of oligomers of up to 15 nucleoside units in lengths. See, for instance, Nucleic Acids Research, 11, pages 5189–5204 and 6225–6242 (1983). Methods for characterizing the chain length and sequence of the oligomers and their interaction with mRNA are also available (Murakami et al, Biochemistry 24, 1985). These methods can be used to prepare sequence specific oligodeoxyribonucleoside methylphosphonates complementary to functional regions of virus mRNAs for present purposes.

DETAILED DESCRIPTION OF THE INVENTION

Figures 1, 2:
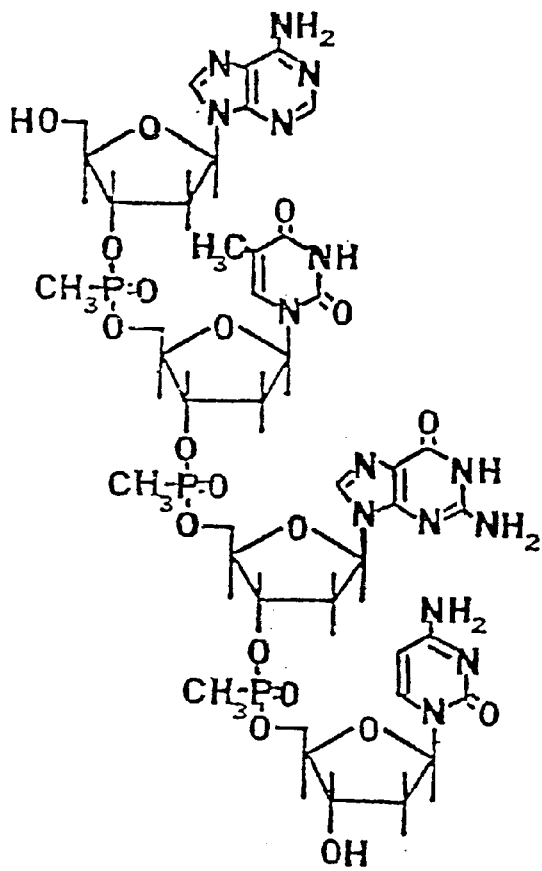
FIG. 1 shows the structure of an oligonucleoside methylphosphonate d-ApTpGpC prior to its being derivatized according to the invention. The symbol p represents (3'–5') methylphosphonate internucleoside bond.
FIG. 2 shows the partial nucleotide sequence of the initiation codon regions of Vesicular stomatitus virus N, NS and G protein mRNAs. The sequence of the complementary oligonucleoside methylphosphonate is shown below each mRNA sequence.

As will be appreciated, the invention contemplates modifying the previously known type of sequence specific oligomers to provide derivatives which will crosslink or otherwise react with nucleic acids, e.g. mRNAs to render them functionally inactive.

The invention is illustrated herein using psoralen or EDTA-derivatized oligodeoxyribonucleoside methylphosphonates. However, as indicated earlier, the invention contemplates the use of a wide variety of functional groups on the oligomers to react in any one of several ways (crosslinking, cleaving, alkylation) with the nucleic acid. Psoralen is typical of the photochemically reactive derivatives which are contemplated for use although other such groups, e.g. angelicin, reactive with the nucleic acid at appropriate wavelengths (e.g. 350–500 nm) may also be used. Substituents capable of alkylation reaction, especially methylation, which do not require photochemical activation for reaction with the nucleic acid may also be used. In this case the alkylating group may or may not leave the oligomer when it attaches to the nucleic acid to inactivate the same. Alkyl halides, haloacetamides such as bromoacetamide, phosphotriesters, etc. may be mentioned as alkylating agents for use herein.

It is also possible to include other functional groups, e.g. a radioactive isotope on the oligomer-for reaction with the nucleic acid.

The EDTA-type derivatives function by cleaving the nucleic acid. As noted, EDTA is preferred for use but other nitrogen containing materials, e.g. azo compounds or nitreens, or transition metal chelating complexes referred to earlier, may be used.

When EDTA is used, iron is also advantageously tethered to the oligomer to help generate the cleaving radicals. The use of EDTA-iron to cleave nucleic acids has previously been disclosed. See Proc. Natl. Acad. Sci., USA, Vol. 82, pages 963–967 and 968–972, February, 1985. However, the concept of attaching the EDTA-iron to a complementary oligomer as contemplated herein to improve selectivity and to permit use in cells is novel and not obvious.

The length of the oligomer and the positioning of the functional group can be varied. The oligomer may comprise, for example, from 3–25 nucleosides and the functional group may be positioned along the chain where it will most effectively react with the nucleic acid. This will depend, in large measure, on the nucleic acid involved and its key site or sites although the optimum position can be readily determined for any particular situation by simple experiment.

It will be appreciated that the actual composition of the derivatives of the invention, e.g. the psoralen or EDTA derivatives, will vary depending on the base sequence of the oligonucleoside alkyl or aryl phosphonate, the sequence itself being determined by the nature of the nucleic acid. Typical derivatives which may be mentioned as exemplified herein include such psoralen-type derivatives as:

d-AMT-pApTGC d-AMT-pTpGCACCAT d-AMT-pTGTTGGTC
d-AMT-pTpGCACCAT
d-AMT(CH$_2$)$_2$NHpTpGTTGGTC
d-AMT(CH$_2$)$_4$NHpTpGTTGGTC
d-AMT(CH$_2$)$_6$NHpTpGTTGGTC
D-AMT-pTpGTTGGTCTTGT

Typical EDTA derivatives include, without limitation, d-EDTA-p-TpGTTGGTC and d-EDTA-pTpGCACCAT.

The derivatives of the invention may be readily prepared by adding the desired functional group, e.g., a photoactivatable or cleaving substituent, to an oligonucleoside methylphosphonate of the required sequence. The latter may be prepared as described in, for example, the above-mentioned U.S. Pat. No. 4,469,863 after which the crosslinking, cleaving or other functional group, e.g. psoralen, EDTA or an equivalent thereof, is attached to the appropriate position of the oligomer.

Before the starting material is prepared, it is, of course, essential to determine the sequence of the nucleic acid which is to be bound or cleaved with the methylphosphonate analogue or equivalent thereof. Such sequence can be determined in conventional fashion using methods and apparatus currently available to those in the art. The sequences for some viral, bacterial and mammmalian cellular nucleic acids are already well established but in other cases it will be necessary to determine these sequences, or at least an essential portion thereof, at the outset.

As noted earlier herein, it appears that the length of the nucleic acid sequence which is determined can be varied. Additionally, it appears that the positioning of the determined sequence in terms of the overall nucleic acid chain can also be varied although, generally speaking, it may be preferable to utilize a sequence at or near the 5' end of the chain or the middle thereof rather than the end as related to the function of the foreign nucleic acid in replication, expression, or translation processes. Normally the sequence determined, and the complementary analogue, should cover at least 3 adjacent bases and preferably 9–15 such bases. This may be varied, however, depending on other factors, e.g. whether a virus or bacteria or a malfunctioning cell is involved and the nature and effect of the nucleic acid of concern.

Once the sequence of the nucleic acid is determined the appropriate complementary alkyl or arylphosphonate analogue, preferably the methylphosphonate analogue, is prepared. This may be accomplished in known fashion by, for example, condensing or esterifying a selected nucleoside which has a 3'-OH group and a protected 5'-OH group with an alkyl or aryl phosphonic acid, the resulting product then being condensed with another nucleoside which has a protected 3'-OH group and a reactive 5'-OH group. The esterification reactions are continued with sequential reaction involving the phosphonic acid group of the preceding product and a selected nucleoside until the desired oligonucleoside is obtained after which protecting group or groups are removed to give the desired oligonucleoside alkyl or arylphosphonate analogue wherein the nucleoside units are linked by isoteric 3'–5' alkyl or arylphosphonate groups. These latter groups are preferably methylphosphonate linking groups although if desired the methyl substituent may be replaced by other alkyl or aryl groups or substituents.

As noted, it is essential for the phosphonate analogue to have a sequence complementary to the foreign nucleic acid involved or targeted. Thus, for example, in the case of a virus DNA where the sequence may be -A-T-C-G, the analogue must have the complementary sequence of -T-A-G-C- so that the sequences are bound together according to the Watson-Crick theory as follows:

$$\begin{array}{cccc} \text{—A} & \text{—T} & \text{—C} & \text{—G—} \\ | & | & | & | \\ \text{—T} & \text{—A} & \text{—G} & \text{—C—} \end{array}$$

Likewise in the case where mRNA having the sequence -UAGC- is concerned, the complementary analogue would be -ATCG-.

It will be appreciated that the oligomer serves two functions, i.e. it exhibits an inhibiting effect of its own on the nucleic acid and it helps to selectively position the functional group at the appropriate spot for most effective reaction with the nucleic acid. The oligomer itself may remain attached to the reactive substituent or the oligomer may split off when the functional substituent reacts with the nucleic acid. In both cases, the oligomer functions to appropriately position the functional or reactive component.

Psoralen is photoreactable, as noted, and requires ultraviolet light for reaction with the nucleic acid. When a photoactivable group is used, it is important to use one which will crosslink or react with the nucleic acid on exposure to light (including laser) but not photodegrade. It appears that any α' β-unsaturated ketone substitution which is ultraviolet light reactable can be used for present purposes. An advantage in using psoralen however, is that it appears to be free from side reactions and any alternative thereto should also preferably be specifically reactive with the nucleic acid.

While various modifications are contemplated, the preferred derivatives of oligonucleoside methylphosphonates contemplated herein contain psoralen or EDTA linked to the 5'-end of a deoxyribooligonucleoside methylphosphonate. The psoralen derivatives have been shown to covalently crosslink to the target mRNA on activation with ultraviolet light to inhibit translation of the mRNA. This inhibition has been obtained at very low concentrations (2.5 $\mu$M) of oligomer and represents a marked improvement (about 80 fold) in efficiency over that of non-derivatized oligomers of the same nucleotide sequence.

The EDTA-derivatives selectively cleave their target nucleic acid to render it biologically nonfunctional. Such derivatives have been shown to cleave mRNA at extremely low oligomer concentrations (~0.1 $\mu$M). This indicates that the EDTA derivative has potential as an antiviral or chemotherapeutic agent.

Both types of derivatized methylphosphonate oligomers, i.e. the crosslinking type represented by the psoralen derivative and the cleaving type represented by the EDTA derivative are particularly useful to molecular biologists and virologists in enabling them to study gene expression in a selective and well defined manner. Thus in addition to their potential value as chemotherapeutic agents, the present derivatives are useful in basic research, and particularly with respect to the control of gene expression.

The invention and advantages thereof are illustrated by the following examples wherein Examples 1 and 2 are given only for comparison purposes while Examples 3–6 are illustrative of the invention.

EXAMPLE 1

Inhibition of VSV mRNA Translation by Oligodeoxyribonucleoside Methylphosphonates (Underivatized)

Methylphosphonate oligomers complementary to the initiation codon regions of Vesicular stomatitis virus (VSV) N, NS and G protein mRNAs were synthesized (see FIG. 2). The results of studies with d-ApACAGACAT which is complementary to the N protein mRNA are shown in Table 1. At low concentrations (50 to 100 µM), the oligomer selectively inhibits N protein synthesis when N, NS and M protein mRNAs are translated simultaneously in a reticulocyte lysate.

Figure 3:
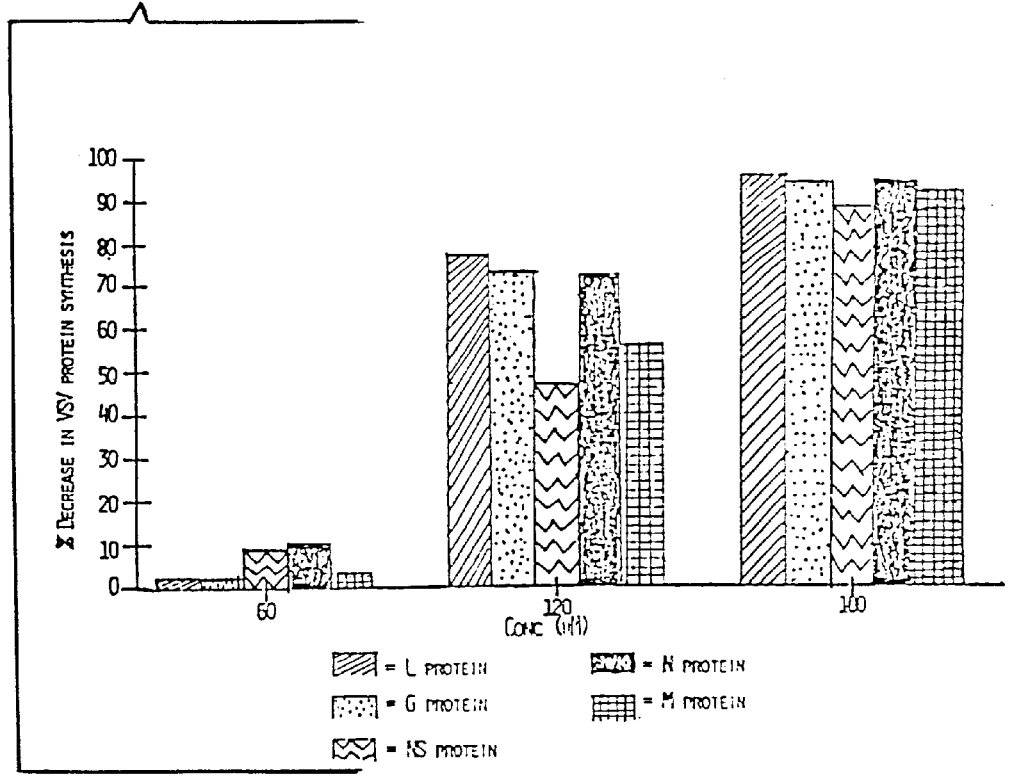
FIG. 3 is a graph showing the effect of d-ACAGACAT on Vesicular stomatitis virus (VSV) protein synthesis in VSV-infected mouse L-cells.

The effects of these oligomers on the synthesis of the five VSV proteins in VSV-infected mouse L-cells were determined. FIG. 3 shows the results obtained with d-Ap ACAGACAT which is complementary to N protein mRNA. In contrast to the results obtained in vitro, the oligomer inhibits synthesis of all five virus proteins to approximately the same extent. At these concentrations, the oligomer has no detectable inhibitory effects on cellular protein synthesis by mouse L-cells and is not cytotoxic to the mouse L-cells as determined from mass culture growth curves. Thus the methylphosphonate oligomer appears to specifically inhibit virus function. The observation that synthesis of all five virus proteins is inhibited may be due to the known requirement of N protein for synthesis of VSV proteins in infected cells.

TABLE 1

Effect of dApACAGACAT on Translation
of Vesicular Stomatitis Virus mRNA
at 30° C. in a Rabbit Reticulocyte Lysate

| Oligomer Concentration | % Inhibition(a) | | |
|---|---|---|---|
| µM | N | NS | M |
| 50 | 23 | −4 | −16 |
| 100 | 33 | −1 | −19 |
| 150 | 77 | 38 | 43 |

(a) Negative sign indicates stimulation of synthesis.

Similar selective inhibition of VSV versus L-cell protein synthesis was also obtained with the methylphosphonate oligomers complementary to the NS and G protein mRNAs. Again inhibition of all five virus proteins was observed. In addition to their effects on VSV protein synthesis, each of the oligomers reduce virus titer approximately one log unit at an oligomer concentration of 150 µM.

The results of these experiments indicate that mRNA translation can be selectively controlled in virus infected cell using the methylphosphonate oligomers.

EXAMPLE 2

Figure 4:
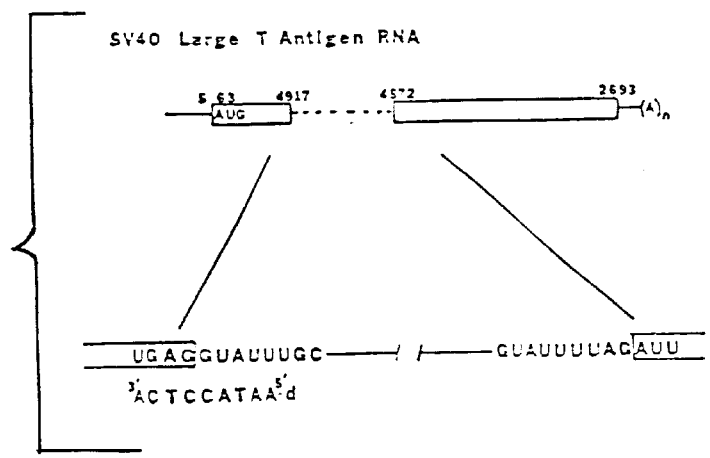
FIG. 4 shows the partial nucleotide sequence of the splice junctions of SV40 large T-antigen pre-mRNA, the sequence of the methylphosphonate oligomer complementary to the donor splice junction being shown below the pre-mRNA sequence.

Inhibitory Effects of Oligodeoxyribonucleoside Methylphosphonates Complementary to the Splice Junction of Virus Pre-mRNA To determine the possibility of controlling gene expression at the level of mRNA processing, oligonucleoside methylphosphoates have been synthesized which are designed to interact with the donor and acceptor splice junction sequences of SV40 large T-antigen precursor mRNA (pre-mRNA). The methylphosphonate oligomers shown in FIG. 4 which are complementary to the donor splice junction of SV40 large T-antigen and to the 5'-terminal sequences of $U_1$ RNA were tested. $U_1$ RNA has been implicated as an agent involved in the splicing of mammalian and viral pre-mRNAs (Nature 283, pp. 220–223, 1980). The effects of the compounds on large T-antigen synthesis in SV40-infected African green monkey kidney cells (BSC40) were determined. The level of large T-antigen was measured by an immunoprecipitation technique using a monoclonal antibody directed against large T-antigen. The splice junction-complementary oligomer, d-AATACCTCA, and the two $U_1$ RNA-complementary oligomers each reduce the level of large T-antigen in the cells, while the non-specific oligomer, d-TTTTTT, had no effect. None of the oligomers had any effect on overall protein synthesis by the BSC40 cells.

A methylphosphonate oligomer, d-TpCCTCCTG, which is complementary to the acceptor splice junctions of Herpes simplex virus type 1 immediate early mRNA 4 and 5 was also prepared. The immediate early proteins are believed to be necessary for regulating the early and late genes of HSV-1 during infection. The oligomer was tested for its effects on ESV-1 in virus infected Vero and human cells. Virus growth was inhibited two log units by 300 µM oligomer. The oligomer selectively inhibits EVS-1 protein synthesis and DNA synthesis in the infected cells. It has no appreciable effect on cellular protein or DNA synthesis. Of particular interest is the effect of d-TpCCTCCTG on the virus proteins. Immediate early mRNA 4 codes for a 68 K protein. This protein is virtually absent in virus infected cells treated with the oligomer.

EXAMPLE 3

Oligodeoxyribonucleoside Methylphosphonates Which Crosslink with mRNA

In the experiments described in Examples 1 and 2, rather high concentrations, 100 to 300 µM, qf oligomers were required to obtain significant inhibitory effects. This is due to the equilibrium nature of the interaction between the oligomer and its target mRNA. According to one aspect of the present invention, more effective inhibition is obtained if the oligomer is crosslinked with the mRNA. This is shown in the present example.

Figure 5:
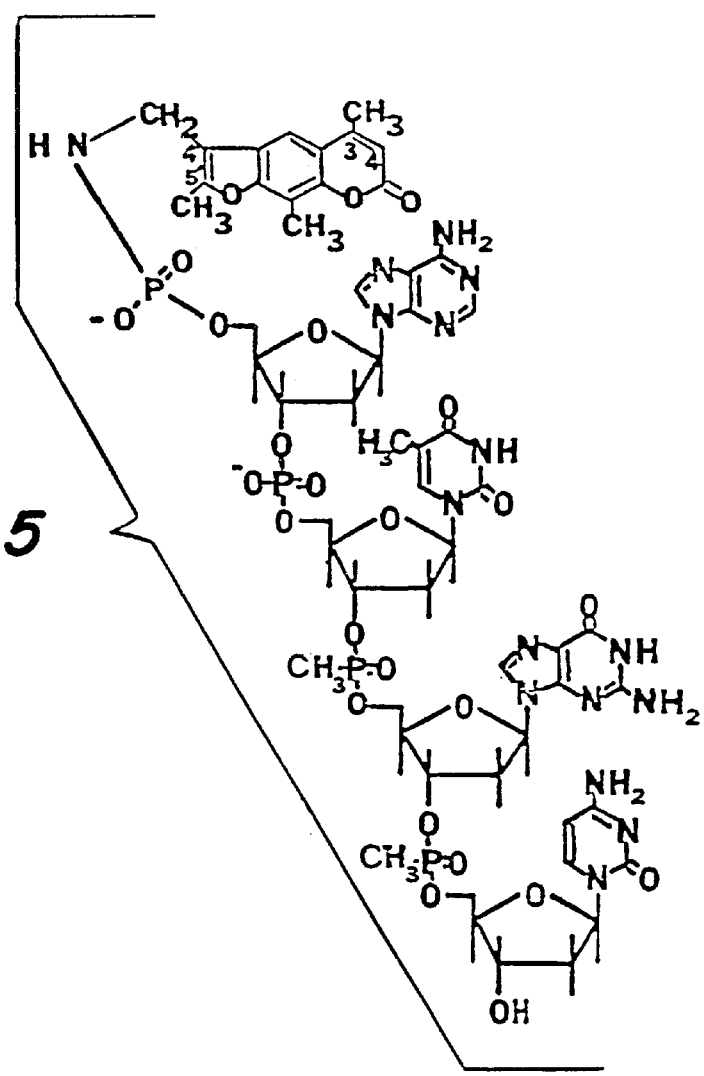
FIG. 5 shows the structure of the oligodeoxyribonucleoside methylphosphonate of FIG. 1 derivatized with trimethylaminomethylpsoralen: d-AMT-pApTpGpC.

Oligonucleoside methylphosphonates derivatized at their 5'-end with aminomethyltrimethylpsoralen (AMT), a photoactivatable crosslinking reagent, were prepared. The structure of one such derivatized oligomer is shown in FIG. 5.

The derivatized oligomer d-PMT-pTp-GCACCAT which is complementary to the initiation codon region of rabbit β globin mRNA and partially complementary to the initiation codon region of α globin mRNA, was prepared. The AMT group is opposite a U residue when the oligomer is complexed with β globin mRNA, whereas it lies opposite a G residue when complexed with α globin mRNA. Since the 3,4 double bond of psoralen can form cyclobutane type adducts with the 5,6 double bonds of U and C residues upon irradiation with 365 nm light, the d-AMT-pTpGCACCAT is able to form a photoadduct with β globin mRNA.

Figure 6:
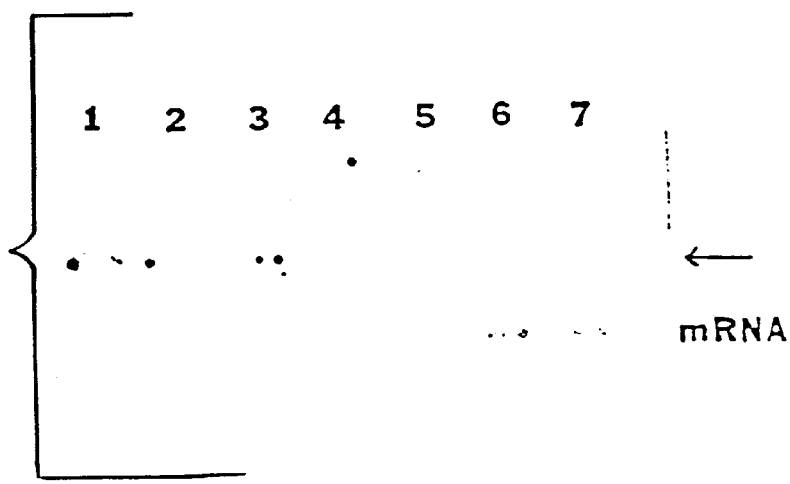
FIG. 6 demonstrates photocrosslinking of (32p) labeled d-AMT-pTpGCACCAT with rabbit globin mRNA after irradiation.

When a mixture of [$^{32}$p]-labeled d-AMT-pTpGCACCAT and rabbit globin mRNA were photoirradiated and then subjected to agarose gel electrophoresis, radioactivity was observed to migrate with the mRNA (see FIG. 6). No radioactivity was observed in the position of mRNA in the absence of irradiation or in the absence of mRNA. No degradation of the mRNA as a result of irradiation was detected in these experiments. These results are consistent with covalent bond formation between the mRNA and the d-AMT-pTpGCACCAT.

With reference to FIG. 6, it is noted that this illustrates photocrosslinking of [$^{32}$p]-labeled d-AMT-pTpGCACCAT (0.0567 µM) with rabbit globin mRNA (0.150 µM) after irradiation at 0° C. The reaction mixtures were electrophoresed on a 2.5% agarose gel. Lanes 1–3: Oligomer and mRNA irradiated for 40, 80 and 120 min. respectively. Lanes 4–7:

Oligomer and mRNA were preannealed for 30 sec. at 100° and then irradiated for 0, 40, 80 and 120 min. respectively. The positions of the top of the gel (+) and the mRNA are indicated.

EXAMPLE 4

The comparative effect of d-AMT-pTpGCACCAT and d-TpGCACCAT on mRNA translation was also determined. After photoirradiation, translation was inhibited 75% (β globin) and 56% (α globin) by only 25 μM AMT-pTp GCACCAT. In contrast, 25 μM d-TpGCACCAT had no inhibitory effect. Comparable inhibition by d-Tp GCACCAT, 70% β globin, 73% α globin, was observed at 200 μM concentration.

The results of the experiments given in Examples 3 and 4 indicate that crosslinking is an effective way to increase the efficiency and selectivity of inhibition by methylphosphonate oligomers. In addition, covalent bond formation between the oligomer and target mRNA offers a way for studying the mechanism of inhibition in a definitive manner.

The results of the foregoing also indicate that the derivatized oligodeoxyribonucleoside methylphosphonates can be used to specifically control gene expression in living cells by interfering with translation or splicing of mRNA. Because the specificity of these compounds resides in their ability to bind to complementary nucleic acid sequences, it should be possible to use nucleic acid sequence information to design novel derivatives of methylphosphonate oligomers which can be used to probe the function of specific proteins in normal, transformed or virus-infected cells. It may also be possible to use these analogs as anti-viral or chemotherapeutic agents.

EXAMPLE 5

Figure 7A:
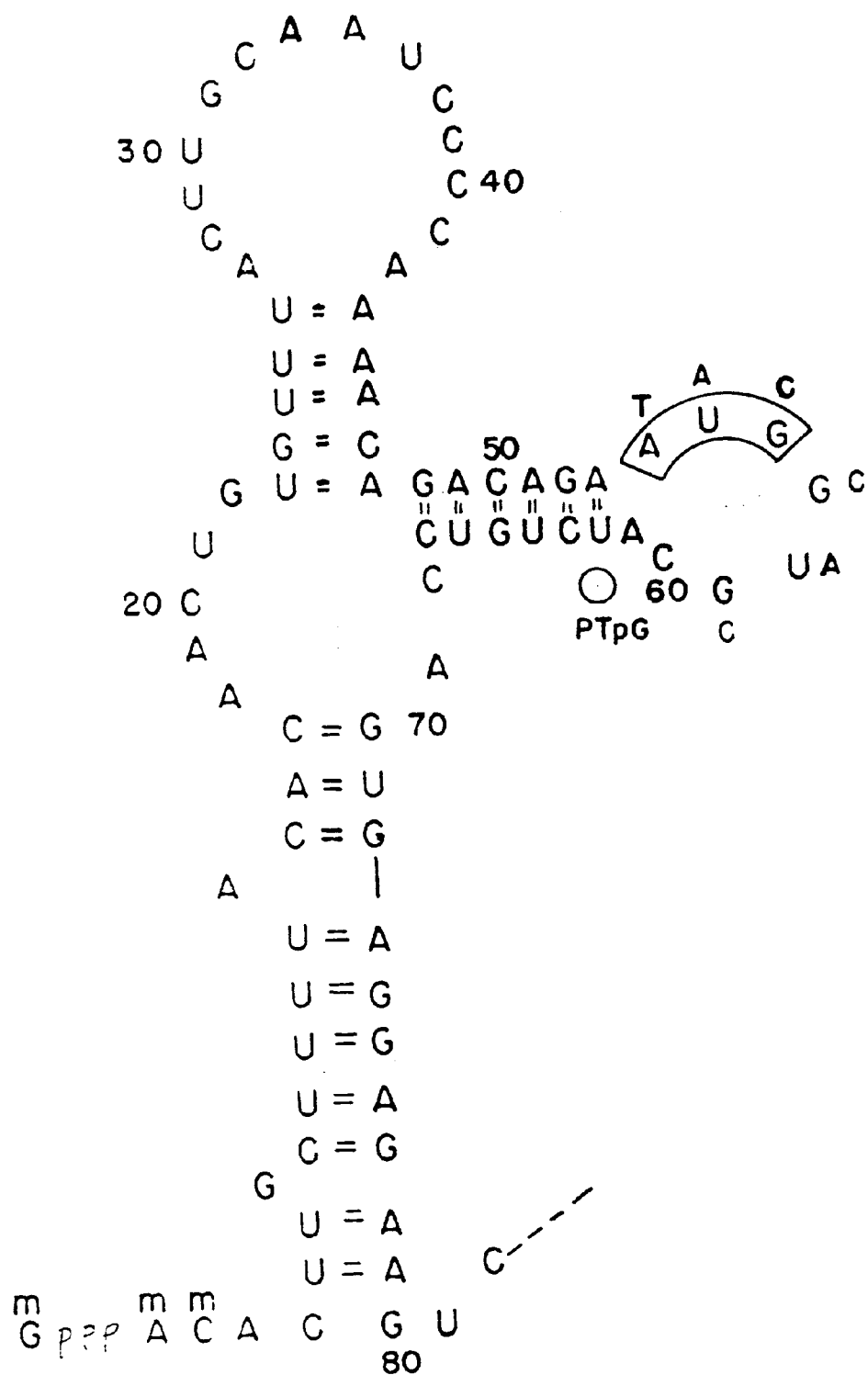
FIG. 7a illustrates a partial nucleotide sequence of α-globin mRNA showing a proposed secondary structure (Pavlakis et al, Cell, 19, 91–102, (1980) and the binding site for d-AMT-pTpGTTGGTC, the aminomethyltrimethylpsoralen group (AMT) being represented by the circle.
Figure 7B:
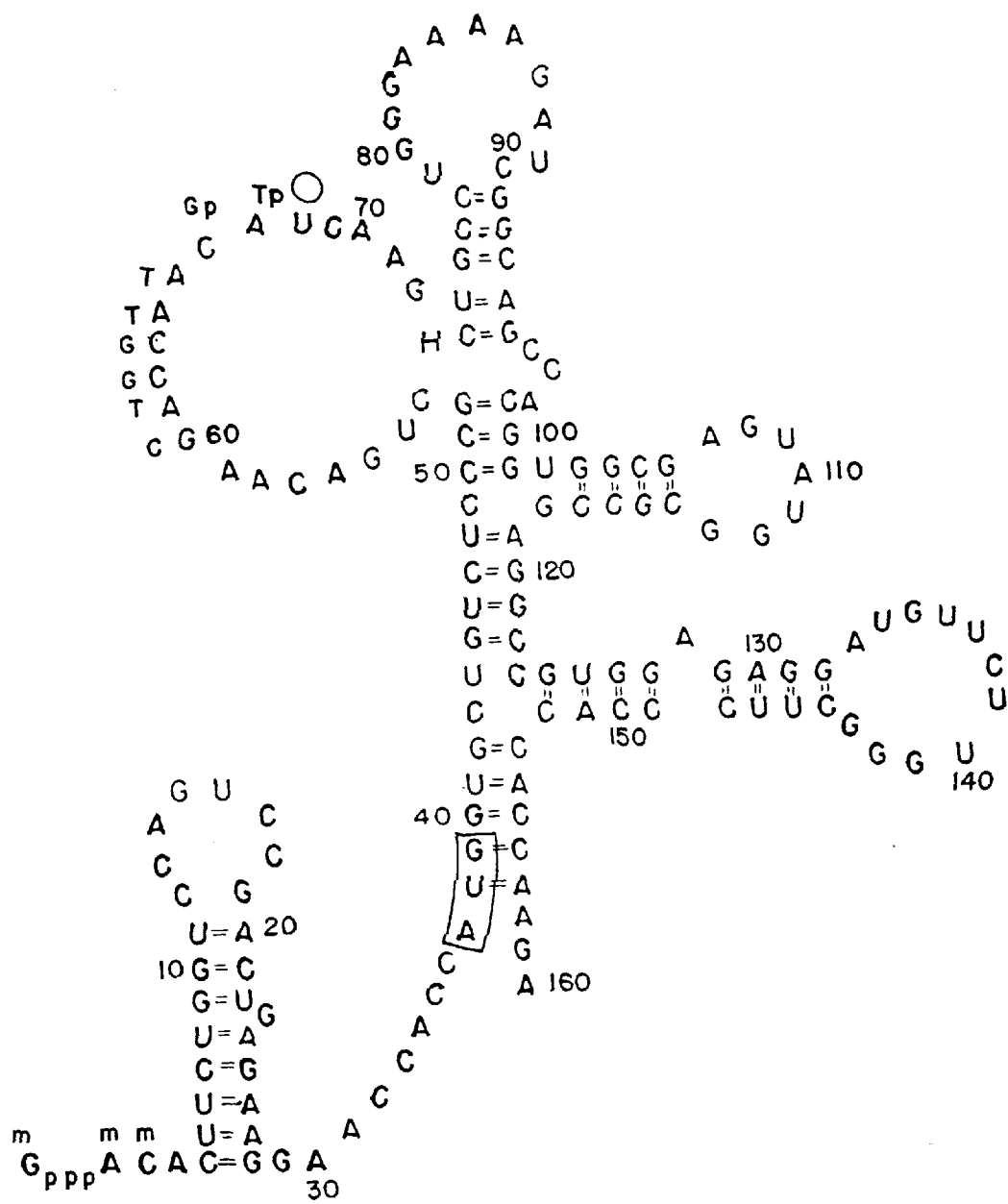
FIG. 7b shows a partial sequence of β-globin mRNA with proposed secondary structure per Pavlakis et al and the binding site for d-AMT-pTpGCACCAT, the AMT group being represented by a circle.

The structures and binding sites for AMT-derivatized oligomers which are complementary to either α and β globin mRNA are given in Table II and illustrated in FIGS. 7a and 7b. As shown, the oligomers are each eight nucleotides in length and begin with the sequence pTpG. The AMT group is linked directly to the 5' phosphoryl group via a phosphoramidate bond or via an aminoethyl or aminohexyl linker arm.

TABLE II

Structures of Aminomethyltrimethylpsoralen Oligonucleoside Methylphosphonate Derivatives

| Oligomer* | Binding Site |
| --- | --- |
| d-AMTpTpGTTGGTC | α globin mRNA nucleotides (60–67) |
| d-AMTpTpGCACCAT | β globin mRNA nucleotides (54–61) |
| d-AMT(CH$_2$)$_2$NHpTpGTTGGTC | α globin mRNA nucleotides (60–67) |
| d-AMT(CH$_2$)$_6$NHpTpGTTGGTC | α globin mRNA nucleotides (60–67) |

*AMT = aminomethyltrimethylpsoralen

The oligomers are complementary to either the coding region of α globin mRNA (nucleotides 60–67) or the initiation codon region of β globin mRNA (nucleotides 54–61). According to the secondary structure model of Pavlakis et al (Cell, 1a, 90–102, 1980) and as shown in FIGS. 7a and 7b, the physical binding sites for both oligomers lie in single stranded loop regions of the mRNAs. In each case the AMT group is lined up opposite uracil residue in the mRNA which is the covalent binding site for the oligomer. In the case of the β globin binding site this uracil is hydrogen bonded to an A residue at the end of a base-paired stem region, whereas in a globin mRNA the uracil residue is free.

Figure 8A:
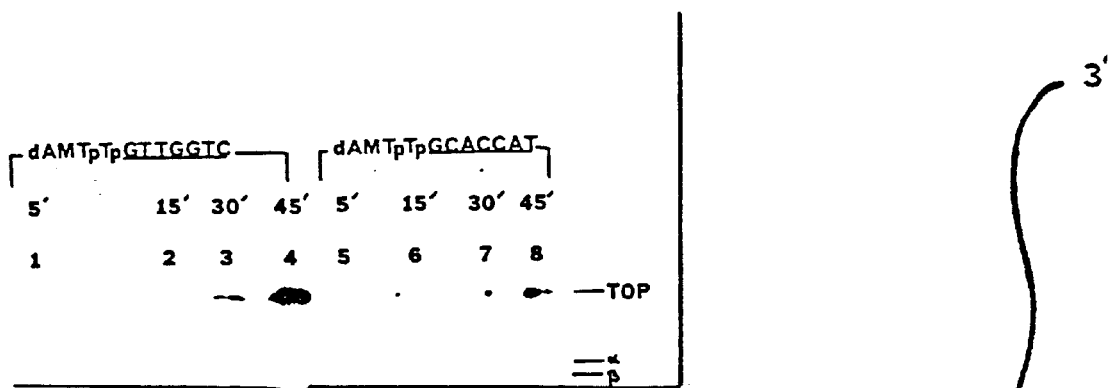
FIG. 8a is an autoradiograph showing the formation of photoadducts between rabbit globin mRNA and d-AMTpTp GTTGGTC mor d-AMTpTpGCACCAT.

Irradiation of [$^{32}$p]-labeled AMT-oligomer and rabbit globin mRNA with 365 nm light at 4° C. results in the formation of covalent adducts between the oligomer and mRNA. As shown in FIG. 8a, d-AMTpTpGTTGGTC binds specifically to α globin mRNA while d-AMTpTp GCACCAT binds specifically to β globin mRNA. The identities of the two mRNAs in the gel were confirmed independently by hybridization with [$^{32}$p]-labeled oligonucleotides whose sequences were complementary to the initiation codon region of α or β globin mRNA. The material at and near the top of the gel represents aggregated α and β globin mRNA which did not move into the gel.

Figure 8C:
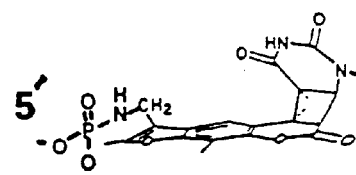
FIG. 8c illustrates a psoralen-derivatized oligodeoxyribonucleoside methylphosphonate crosslinked with a uridine residue of mRNA.
Figure 8B:
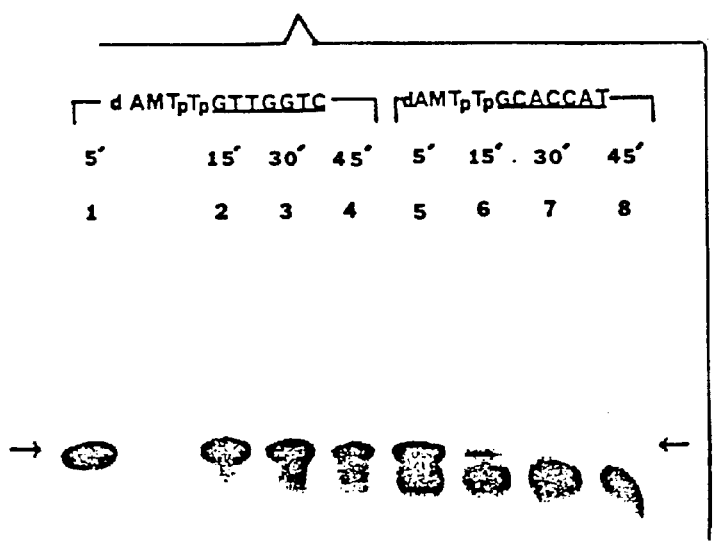
FIG. 8b is another autoradiocraph which shows the photoreactions of d-AMTpTGTTGGTC and d-AMTpTp GCACCAT.

The oligomers themselves undergo a photochemical reaction when irradiated at 365 nm as shwon in FIG. 8b. A new, faster moving material appears as the time of irradiation increases. d-AMTpTpGCACCAT is almost completely converted after 30 min. whereas approximately 50% of d-AMTpTpGTTGGTC is reacted after 45 min. Examination of molecular models shows that the psoralen ring system can stack on the thymine base with the 4',5' double bond of the psoralen furan ring below the 5,6 double bond of the thymine. Proton NMR spectra of a model compound, d-AMTpT, suggest that such stacking does occur in aqueous solution. Irradiation of the molecule in this conformation could thus lead to cyclobutaine ring formation between the psoralen group and the thymine residue at the 5' end of the oligomer. When d-AMTpT is irradiated, the intensity of the UV spectrum diminishes. The UV spectrum is restored by irradiation at 254 nm. This behavior is consistent with the known properties of cyclobutane adducts formed between psoralen and thymine base residues (Cimino et al, Ann. Rev. Biochem. 54, 1151–1193, 1985).

As shown in FIG. 8a, d-AMTpTpGTTGGTC appears to crosslink more efficiently with its target mRNA than does d-AMTpTpGCACCAT. This behavior may be the result of differences in the binding sites for the two oligomers. As shown in FIGS. 7a and 7b, the binding site for d-AMTpTp GCACCATlies adjacent to a stem region. In order to crosslink to uracil #62, the stem must open up which may be energetically unfavorable. In contrast uracil residue #68 of α globin mRNA is free to crosslink with the psoralen of d-AMTpTpGTTGGTC.

The decreased efficiency of crosslinking by d-AMTpTp GCACCAT may also reflect its conversion to a new product, possibly intramolecular cyclobutane adduct, during the course of irradiation. A separate experiment showed that d-AMTpTpGCACCAT, which had been pre-irradiated at 365 nm for 45 min., underwent little or no crosslinking when it was subsequently irradiated in the presence of globin mRNA. Thus the photoconversion of d-AMTpTp GCACCAT to an inactive product competes effectively with the crosslinking reaction resulting in a lowered efficiency of covalent adduct formation with the globin mRNA. Examination of molecular models shows that if an intramolecular cyclobutane type adduct is formed by d-AMTpTp GCACCAT, the psoralen ring of this adduct is now fixed in an orientation unfavorable to crosslinking with the uracil residue fo the mRNA strand.

The effect of linker length on the efficiency of the crosslinking reaction is not completely defined. Examination of molecular models suggest that a linker containing between 3 to 7 atoms facilitates crosslinking by allowing the 3,4 double bond of the psoralen pyrone ring to lie closer to the uracil 5,6 double bond. This increased proximity decreases the re-orientation of the uracil required for crosslinking.

The following additional details are provided with respect to FIGS. 8a and 8b:

FIG. 8a shows the formation of photoadducts between rabbit globin mRNA and d-AMTpTpGTTGGTC (lanes 1–4) or d-AMTpTpGCACCAT (lanes 5–8). Aqueous solutions of mRNA (80 nM) and [$^{32}$p]-labeled oligomer (100 nM) were irradiated at 365 nm at 4° C. for 5 min. (lanes 1,5) 15 min. (lanes 2,6), 30 min. (lanes 3,7), and 45 min. (lanes 4,8). The reaction mixtures were electrophoresed on a 7% acrylamide/ 0.25% agarose gel which contained 7 M urea at 500 V for 4 hrs. The gel was autoradiocraphed at −80° C. for 16 hrs. The top of the gel and the positions of α and β globin mRNA, which were determined by staining the gel with ethidium bromide, are indicated at the side of the autoradiogram. The material in the lower part of the gel is unreacted oligomer.

FIG. 8b shows the photoreactions of d-AMT-pTGTTGGTC (lanes 1–4) and d-AMTpTpGCACCAT (lanes 5–8). Aqueous solutions of the [$^{32}$p]-labeled oligomers were irradiated at 365 nm at 4° C. for 5 min. (lanes 1,5), 15 min. (lanes 2,6), 30 min. (lanes 3,7) and 45 min. (lanes 4,8). The reaction mixtures were electrophoresed on a 20% acrylamice gel which contained 7 M urea at 800 V for 2 hrs. The gel was autoradiographed at −80° C. for 16 hrs. The position of the starting oligomers are indicated at the sides of the autoradiogram.

FIG. 8c, as noted earlier, illustrates how a psoralen-derivatized oligodeoxyribonucleoside methylphosphonate crosslinks with a uridine residue of mRNA.

Figure 9:
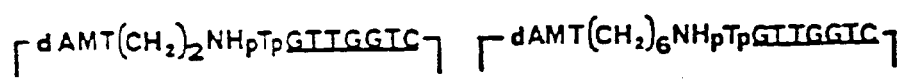
FIG. 9 shows the formation of photoadducts between rabbit globin mRNA and d-AMT($CH_2$)$_2$NHpTpGTTGGTC or d-AMT($CH_2$)$_6$NHpTpGTTGGTC.

As shown in FIG. 9, d-AMT(CH$_2$)$_2$NHpTpGTTGGTC and d-AMT(CH$_2$)$_6$NHpTpGTTGGTC both specifically crosslink with α globin mRNA at an oligomer concentration of 2.7 nM. Separate experiments did not detect crosslinking with 2 nM d-AMTpTpGTTGGTC. Thus, the oligomers containing aminoalkyl linkers appear to crosslink more efficiently than the oligomer in which AMT is attached directly to the oligomer. Because both oligomers shown in FIG. 9 have the same specific activity, the results show that d-AMT(CH$_2$)$_2$NHpTpGTTGGTC crosslinks more efficiently than d-AMT(CH$_2$)$_6$NHpTpGTTGGTC. It appears that linker length and oligomer chain length have sorme effect on the efficiency of the photocrosslinking reaction.

A more detailed explanation regarding FIG. 9 is as follows:

This figure shows the formation of photoadducts between rabbit globin mRNA and d-AMT(CH$_2$)$_2$NHpTpGTTGGTC (lanes 1–5) or d-AMT(CH$_2$)$_6$NHpTpGTTGGTC (lanes 6–9). Aqueous solutions of mRNA (100 nM) and [$^{32}$p]-labeled oligomer (2.7 nM) were irradiated at 365 nm at 4° C. for 0 min. (lane 1), 5 min. (lanes 2,6), 15 min. (lanes 3,7), and 30 min. (lanes 4,8). The oligomers were also irradiated in the absence of mRNA for 30 min. (lanes 5,9). The reaction mixtures were electrophoresed on a 7% acrylamide/0.25% agarose cel which contained 7 M urea at 500 V for 4 hrs. The gel autoradiographed at −80° C. for 16 hrs. The top of the gel and the positions of α and β globin mRNA are indicated along the side of the autoradiogram.

The effects of d-AMTpTpGTTGGTC and d-AMTpTpGCACCAT on cell-free translation of rabbit globin mRNA in a reticulocyte lysate system are shown in Table III. The oligomer and mRNA were irradiated for 60 min. at 0° C. prior to translation, which was carried out at 37° C. Little or no inhibition of translation by the oligomers was observed in the absence of irradiation. Translation of globin mRNA irradiated in the presence of as little as 0.5 μM oligomer was inhibited to a significant extent. Inhibition of both α and β globin mRNA translation was observed. This lack of specificity may reflect the coordination of translation of α and β globin mRNA in the reticulocyte lysate. In any case, the inhibition does not appear to be due to degradation of mRNA. Irradiation of globin mRNA in the presence of 10 μM oligomer for 60 min. does not result in any detectable hydrolylsis of the mRNA as assayed by polyacrylamide gel electrophoresis.

TABLE III

Effects of AMT-Derivatized Oligonucleoside Methylphosphonates on Translation of Rabbit Globin mRNA in a Rabbit Reticulocyte Lysate at 37° C.[a]

| Oligomer | Concentration μM | Irradiation 365 nm | % Inhibition[b] α globin | β globin |
|---|---|---|---|---|
| d-AMTpTpGTTGGTC | 2.5 | − | 12 | 7 |
| | 10.0 | − | 3 | −13 |
| | 0.5 | + | 23 | 14 |
| | 2.5 | + | 47 | 43 |
| | 10.5 | + | 30 | 50 |
| d-AMTpTpGCACCAT | 10.0 | − | 9 | 13 |
| | 0.5 | + | 18 | 28 |
| | 2.5 | + | 48 | 49 |
| | 10.0 | + | 42 | 34 |

[a]The oligomer and globin mRNA (0.04 to 0.08 μM) were irradiated at 0° C. for 60 min prior to translation at 37° C.
[b]A minus sign (−) indicates stimulation of translation.

The above results demonstrate that AMT derivatized oligonucleoside methyphosphonates can photocrosslink with mRNA in a sequence specific manner, even at very low oligomer concentrations and thus inhibit mRNA translation. By adjusting the linker length and oligomer chain length it is possible to optimize the specificity of the crosslinking reaction for any particular situation. Furthermore, since the AMT-derivatized oligomers appear to be taken up intact by mammalian cells in culture, the oligomers should be useful to inhibit the translation of virus mRNA in virus-infected cells. Tests with Vesicular Stomatitis virus (VSV) indicate that an AMT-derivatized oligomer complementary to VSV N protein mRNA photocrosslinks with VSV mRNA but not rabbit globin mRNA.

EXAMPLE 6

Figure 10:
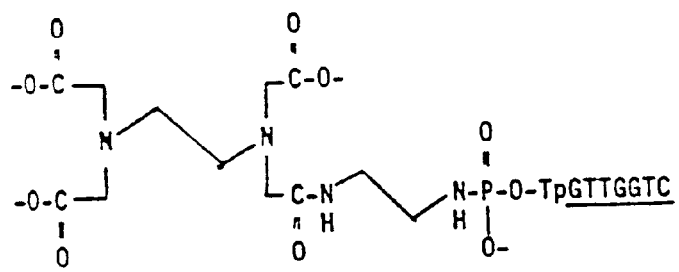
FIG. 10 structurally illustrates an EDTA-derivatized oligodeoxyribonucleoside methylphosphonate.

Using the method of Chu et al (Proc. Natl. Acad. Sci. USA, 82, 963–967, 1985), the EDTA-derivatized methylphosphonate oligomer shown in FIG. 10 was prepared. This oligomer is complementary to nucleotides 60–67 in the coding region of rabbit a globin mRNA. The stability of the oligomer was examined in acueous solution. The oligomer was found to be stable indefinitely in aqueous ethanol solutions at −20° C. In tris buffer at pH 8.0, the oligomer undergoes autodegradation in the presence of 4 mM dithiothreitol and 10 μM ferrous sulfate. No degradation was observed in the presence of FeSO$_4$ alone or DTT alone. The halflife of autodegradation reaction was approximately 30 min. at room temperature. It appears that autodegradation involves cleavage of the single phosphodiester linkage in the oligomer. Little or no cleavage of the methylphosphonate linkages was observed.

In preliminary experiments relating to the effect of this oligomer on rabbit globin mRNA the oligomer was incubated with the mRNA in the presence or absence of FeSO$_4$/ DTT at 0° or 25° C. The mRNA was then electrophoresed on a polyacrylamide gel and the gel then probed with [$^{32}$p]-labeled oligonucleotides complementary to the initiation codon regions of α or β globin mRNA. Under these conditions there appeared to be no significant hydrolysis (10% or more) of the α globin mRNA.

EXAMPLE 7

Effect of EDTA-Modified d-TpGCACCAT on Rabbit Globin mRNA

Figure 11:
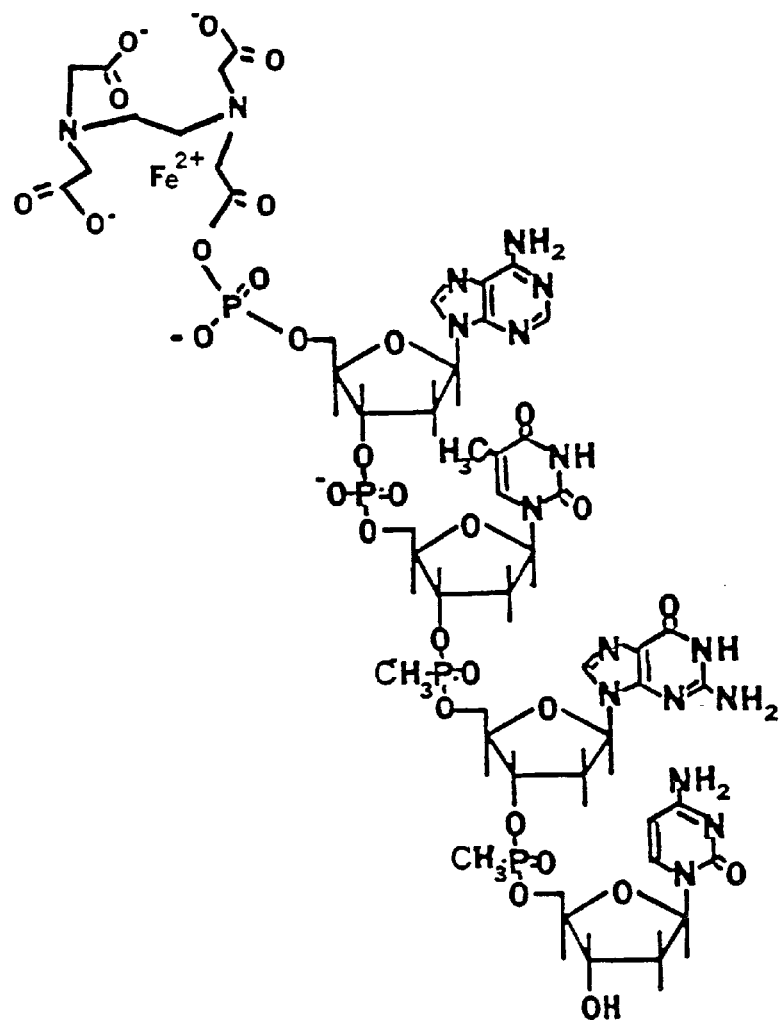
FIG. 11 shows an EDTA-$Fe^{2+}$-derivatized oligonucleoside methylphosphonate (EDTA-$Fe^{2+}$-d-ApTpGpC)

This Example describes the preparation of an EDTA-derivatized oligodeoxyribonucleoside methylphosphonate starting with an octamer, d-TpGCACCAT. The general structure of the EDTA-modified product is shown in FIG. 11.

Figure 12:
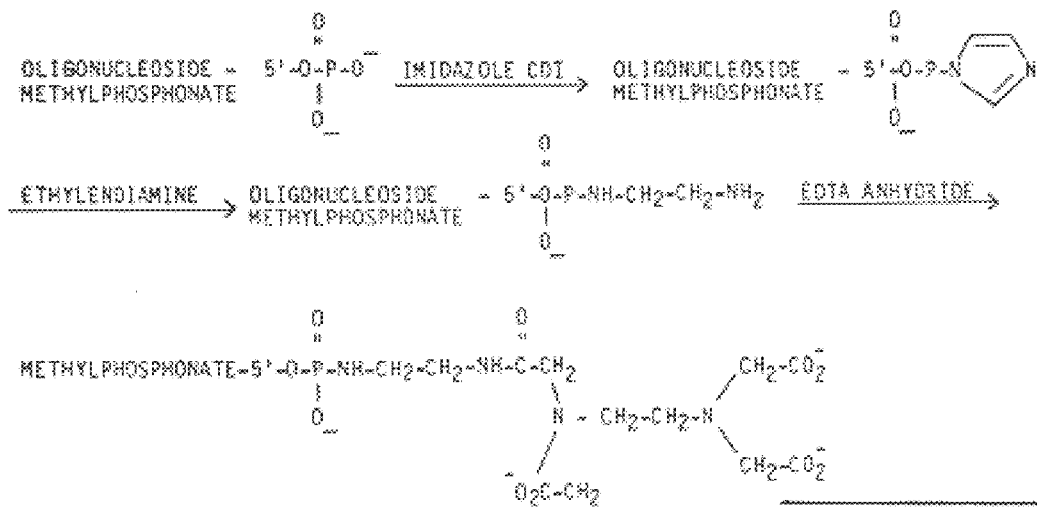
FIG. 12 illustrates a synthesis scheme for the preparation of the EDTA-$Fe^{2+}$ modified oligonucleoside methylphosphonates.

The octamer d-TpGCACCAT, which is complementary to nucleotides 37–43 of α-globin mRNA and nucleotides 54–61 of β-globin mRNA, was converted to its EDTA derivative by the method of Chu and Orgel (Proc. Natl. Acad. Sci., 82, 9§© (1985)) as shown in FIG. 12. The EDTA-pTpGCACCAT was purified by polyacrylamide gel electrophoresis.

The derivatized oligomer was incubated with rabbit globin mRNA. and the reaction mixture was subjected to agarose gel electrophoresis. More specifically, reaction mixtures containing 0.25 µM rabbit globin mRNA were treated as follows: lane 2—no treatment; lane 3—incubated with 1M aqueous piperidine at 37° C. for 60 min.; lanes 4 and 5—incubated with 0.1 µM oligomer at 22° for 60 min.; lanes 6 and 7—incubated with 0.1 µM oligome+ at 37° C. for 60 min. After incubation, the reaction mixtures were applied to an agarose gel and electrophoresed. The gel was stained with ethidium bromide and photographed. The results are shown in FIG. 13.

Figure 13:
FIG. 13 is an illustration of an agarose gel showing hydrolysis of rabbit globin mRNA by EDTA-$Fe^{2+}$ modified d-TpGCACCAT.

As shown in FIG. 13, under the indicated conditions, the mRNA was hydrolyzed by the oligomer. Significantly more hydrolysis occurred at 22° C. (lanes 4 and 5) than at 37° C. (lanes 6 and 7). This behavior is consistent with the ability of the oligomer to bind more strongly to the mRNA at lower temperatures. In these experiments, the mRNA concentration was 0.25 µM whereas the oligomer concentration was 0.1 µM. The complete hydrolysis of the mRNA observed at 22° C. thus shows that oligomer functions in a catalytic manner at very low concentrations. The results of these experiments indicate that EDTA-$Fe^{2+}$ derivatized oligodeoxyribonucleoside methylphosphonates are very effective inhibitors of mRNA function even at low (<1 µM) concentrations. This indicates considerable potential of the derivitized oligomers for use as chemotherapeutic agents.

It will be appreciated from the foregoing that various modifications may be made in the invention as exemplified above. Thus, for example, the chain length of the oligomers may be varied as desired and the nature and positioning of the crosslinking or cleaving group may also be varied. For example, the effectiveness of the derivative may be changed by varying the positioning of the EDTA or psoralen group so that the group is placed either at the 5'-end of a methylphosphonate oligomer which contains no phosdhociester group or by placing the group in the middle or at the 3'-end of the oligomer.

Various available procedures may also be used to prepare the derivatives of the invention. Thus, for example, the synthesis of methylphosphonate oligomers derivatized at their 5'-end with psoralen may be accomplished by first preparing the imidazolid of the oligonucleoside methylphosphonate by reaction with imidazole and 1-ethyl-3-(3-dimethylaminopropyl) carbodiimide following the procedure of Chu et al (Nucleic Acid Res., 11, 6513–6529). The imidazolide is then reacted with aminomethyltrimethylpsoralen (AMT) to give the desired product. This series of reactions takes approximately two days to complete. It may be occasionally found that conversion of oligonucleoside methylphosphonate to the desired product is incomplete. Because the oligomer and product have the same net charge, it is difficult to separate them by gel electrophoresis or DEAE cellulose chromatography. However, it has been found that d-pNp(Np)$_n$N can be converted directly to its aminomethyltrimethylpsoralen derivative, d-AMT-pNp(Np)$_n$N, by reaction with aminomethyltrimethylpsoralen and carbodiimide in 2,6-lutidine buffer, pH 7.0. The reaction is essentially complete within 6 hours at room temperature. The product is readily purified by DEAE cellulose chromatography.

Using this procedure aminomethyltrimethylpsoralen derivatives, d-AMT-pNp(Np)$_n$N, have been synthesized on a 60 nmol scale with an overall isolated yield of 60% and it is believed that these reactions can be scaled up to at least 1 µmol of starting oligomer to provide approximately 600 nmols of derivatized oligomer.

This derivatized oligomer appears to inhibit mRNA translation in the concentration range of 1 to 10 µM. Typically, amounts of the AMT derivatized octanucleoside methylphosphonate, d-AMTpTpGCACCAT, in this range will form a covalent adduct with rabbit globin mRNA when irradiated at 365 nm.

Methods for attaching EDTA or psoralen, or the like to the oligonucleotide are known and these can be used for present purposes to place a variety of functional groups, reactive with RNA, on the selected oligomer sequences. For example, it is known how to attach EDTA covalently to the 5' terminus of a deoxynucleotide sequence and it is also known that the resulting adduct can be used for sequence specific cleavage of DNA. See, for example, papers by Chu et al and Dreyer et al in Proc. Natl. Acad. Sci. USA, Vol. 82, pages 963–967 and 968–972, February 1985.

It will be appreciated that the psoralen and the EDTA-derivatized methylphosphonate oligomers serve to illustrate the broad aspsects of the invention. Thus, it is shown that the psoralen derivative, or its equivalent, can be used to covalently crosslink to the target nucleic acid upon activation with ultraviolet light. This can be done to, for example, inhibit translation of mRNA at low concentrations of the oligomer. Likewise, it is shown that the oligomers modified with EDTA or the like can be used to selectively cleave the target nucleic acid and thus render it biologically nonfunctional.

A specific feature of the invention is the manner in which the psoralen, EDTA or other crosslinking, cleaving or functional group is attached to the oligonucleoside. According to the invention, the functional group is linked to the P atom of a phosphate group through the N atom of an aminomethyl group (—NH—$(CH_2)_n$— so as to provide a phosphoramidate linkage:

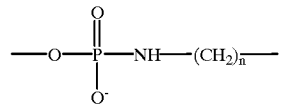

n is a whole number of from 1–8, which joins the oligomer and functional group as follows:

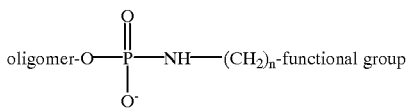

The phosphoramidate linkage preferably also includes a further amino group between the (CH$_2$) methylene and the functional group to provide the following:

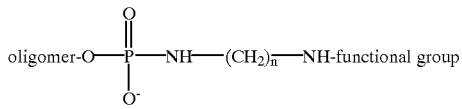

Thus, for example, in the case of EDTA-derivatized oligomer, the EDTA is linked to the P atom of a phosphate group by the linkage —NH—(CH$_2$)$_n$—NH— via a carboxylate group of the EDTA to provide:

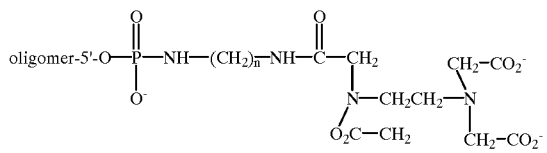

Similarly, psoralen may be linked to a 5'-phosphate as follows:

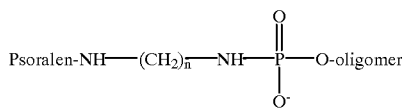

These linkages are substantively different from the linkages disclosed in U.S. Pat. No. 4,835,263 where functional groups are linked to either a sugar or phosphate group at the 5'-or 3'-end of an oligomer through alkylene or alkyleneoxy groups. In the case of alkyleneoxy linkers to phosphate groups, a phosphodiester bond is formed as follows:

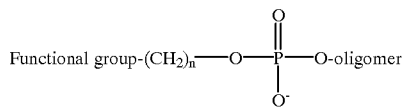

The resulting phosphodiester bond is subject to rapid degradation by nucleases present in serum, cells or cell culture medium. Thus, the derivatized oligomers based on such linkages would be more susceptible to degradation before the oligomer could reach its target within the cell.

On the other hand, the phosphoramidate linkage used for the derivatives of the present invention is not hydrolyzed by nucleases and is thus very stable. This is shown by the fact that psoralen derivatized oligonucleoside methylphosphonates according to the invention can be recovered intact from both cell culture medium and from the mammallan cells in culture after incubation for at least 8 hours at 37° C.

While the invention has been illustrated using, for example, psoralen derivatized methyl phosphonate oligomers, which include thymidine (T), it will be appreciated that, as an example, this base may be replaced by uridine (U), e.g. 2'-deoxyuridine. In some cases, this may provide an increased crosslinking effect.

Another modification according to the invention involves using a ribonucleoside backbone which includes a 2'-lower alkoxy substituent, particularly methoxy, in place of a 2'-O-deoxyribonucleoside backbone. The 2'-O-methylribonucleoside methylphosphonates appear to form more stable duplexes with an RNA target molecule than do the corresponding 2'-deoxyribonucleoside methylphosphonates. This indicates that, for example, psoralen derivatized 2'-O-methylribonucleoside methylphosphonates provide increased crosslinking and thus increased inhibitory effects compared to the 2'-deoxyribonucleoside methylphosphonates. This offers the advantage of using lower oligomer concentrations than might be feasible with the corresponding 2'-deoxyribonucleoside methylphosphonates.

As illustrative of the above, it is noted that oligonucleoside methylphosphonates containing 2'-O-methylribonucleoside units have been synthesized using 3'-O-N,N-bis-(diisopropyl)aminomethylphosphonamidite synthons. A pentamer, r-U$^m$pI$^m$$_A$$^m$$_U$$^m$$_C$ [1], where m indicates a 2'-O-methylnucleoside and p represents a methylphosphonate linkage, and r-GAUCA [11], form a duplex whose T$_m$ is 16° C. In contrast, the T$_m$ of the corresponding duplex formed by the penta-2'-deoxyribo- nucleoside methylphosphonate, d-TpGpApTpC [111], and [11] is 9° C. or less. The increased stability of duplex formed by [1]+[11] is believed to be due to the ability of [1] to readily assume an A-type conformation. This indicates that 2'-O-methylribonucleoside methylphosphonates would form more stable duplexes with their mRNA targets than do 2'-deoxyribonucleoside methylphosphonates.

The following provides further illustrations of useful aspects of the invention:

Oligo-2'-deoxyribonucleoside methylphosphonates which are derivatized at their 5'-ends with 4'-[[N-(aminoethyl)amino]methyl]-4,5'8-trimethylpsoralen, (ae) AMT, or 3-[(2-aminoethyl)carbamoyl]-psoralen, (ae)CP, form cyclobutane adducts with target strand T or U residues when duplexes formed by these derivatized oligomers and complementary single stranded DNA or RNA oligonucleotide targets are irradiated at 365 nm. The psoralen ring can either stack on the terminal base pair formed between the oligomer and its target DNA (n position) or it can intercalate between the last two pairs of the oligomer-DNA duplex (n–1 and n positions), and the position of the crosslinking site can affect the extent of the crosslinking reaction. Thus, oligomers derivatized with (ae)AMT crosslink most efficiently to a thymidine at the n+1 position whereas oligomers derivatized with (ae)CP crosslink most efficiently to thymidines located at the n or n–1 positions in the target. Substitution of deoxyuridine for thymidine residues in the (ae)AMT-derivatized methylphosphonate oligomers, results in increased crosslinking. This may be due to increased stability of the duplex resulting from reduced Van der Waals interactions between the S$_p$ phosphonate methyl group and the thymidine 5-methyl group of the oligomer. Psoralen-derivatized oligomers have also been further derivatized with tetramethylrhodamine. This fluorescent probe is attached via a phosphoramidate linkage to the last internucleotide bond at the 3'-end of the oligomer and could be useful in detecting the interaction of the oligomers with target nucleic acids inside living cells.

(ae)AMT-derivatized oligo-2'-deoxyribonucleoside methylphosphonates (12-mer, 16-mer and 21-mer) complementary to a putative loop/stem in the coding region of vesicular stomatitis virus (VSV) M protein mRNA (m-mRNA) each specifically crosslink to M-mRNA when a mixture of the oligomer (1 $\mu$M) and poly adenylated RNA (1.3 $\mu$g) isolated from VSV-infected mouse L cells are irradiated at 365 nm in TMK buffer at 22° C. In contrast, a (ae)AMT-12 mer complementary to a sequence in the coding region of VSV N-mRNA did not crosslink to any of the VSV mRNAs under these conditions. The binding site for this oligomer appears to be a stem structure as predicted by computer folding of the VSV N-mRNA. The M-mRNA specific (ae)AMT-oligomers crosslink with RNA in VSV-infected mouse L-cells when oligomer (1 μM) treated cells are irradiated at 365 nm for 5 minutes at room temperature. Crosslinking was not observed in VSV-infected cells which were not irradiated nor was crosslinking observed when uninfected mouse L-cells were irradiated in the presence of the oligomers. The 21-mer crosslinked approximately 4 times more extensively than did the 12-mer. The results of these experiments indicate that (ae)AMT-methylphosphonate oligomers are taken up by VSV-infected cells and crosslink with VSV RNA. Thus, these oligomers should be useful to selectively inhibit translation of targeted mRNAs in cells.

Inasmuch as various modifications may be made in the invention, the scope of the invention is defined in the following claims wherein:

What is claimed is:

1. An oligonucleoside alkyl or arylphosphonate analogue which is complementary to the sequence of a target nucleic acid and includes a functional group X which reacts with the target nucleic acid to render the target nucleic acid inactive or nonfunctional, the functional group X being joined to the P atom of a phosphate group of the oligonucleoside through a $-NH-(CH_2)_n-$ linkage or a $-NH-(CH_2)_2-NH-$ linkage where n is 1 to 8 to provide a compound represented by the formula:

$$\text{oligonucleoside-O}-\overset{\overset{\displaystyle O}{\|}}{\underset{\displaystyle O^-}{P}}-NH-(CH_2)_{\overline{n}}-X \quad \text{or}$$

$$\text{oligonucleoside-O}-\overset{\overset{\displaystyle O}{\|}}{\underset{\displaystyle O^-}{P}}-NH-(CH_2)_{\overline{n}}-NH-X.$$

* * * * *